(12) United States Patent
Härmä

(10) Patent No.: US 8,956,877 B2
(45) Date of Patent: Feb. 17, 2015

(54) SEPARATION-FREE ASSAY METHOD

(75) Inventor: Harri Härmä, Turku (FI)

(73) Assignee: Aqsens Oy, Helsinki (FI)

( * ) Notice: Subject to any disclaimer, the term of this patent is extended or adjusted under 35 U.S.C. 154(b) by 1045 days.

(21) Appl. No.: 12/186,961

(22) Filed: Aug. 6, 2008

(65) Prior Publication Data

US 2009/0017466 A1    Jan. 15, 2009

Related U.S. Application Data

(60) Provisional application No. 60/774,608, filed on Feb. 21, 2006.

(30) Foreign Application Priority Data

Feb. 21, 2006    (FI) ...................................... 20060166

(51) Int. Cl.
  *G01N 21/76*    (2006.01)
  *G01N 33/58*    (2006.01)
(52) U.S. Cl.
  CPC .................................. *G01N 33/582* (2013.01)
  USPC .......... 436/172; 435/7.1; 435/7.92; 435/7.93; 435/7.94; 436/164; 436/501; 436/518
(58) Field of Classification Search
  None
  See application file for complete search history.

(56) References Cited

U.S. PATENT DOCUMENTS

| | | | | |
|---|---|---|---|---|
| 4,256,834 A | | 3/1981 | Zuk et al. | ........................... 435/7 |
| 5,674,699 A | * | 10/1997 | Saunders et al. | ............. 435/7.93 |
| 6,420,183 B1 | * | 7/2002 | Krahn et al. | ................... 436/164 |
| 2004/0253593 A1 | | 12/2004 | Cai et al. | ........................... 435/6 |

FOREIGN PATENT DOCUMENTS

WO    WO 2005/040756    *    5/2005

OTHER PUBLICATIONS

Szollosi et al., Application of Fluorescence Resonance Energy Transfer in the Clinical Laboratory: Routine and Research, Cytometry (Communications in Clinicl Cytometry) 34: pp. 159-179, 1998.*
Bazin et al., Homogeneous time resolved fluorescence resonance energy transfer using rare earth cryptates as a tool for probing molecular interactions in biology, Spectrochimica Acta Part A 57 (2001), pp. 2197-2211.*
Diamandis et al., Immunoassay, Academic Press, Chapter 11, The Avidin-Biotin System, pp. 237-267, 1996.*

* cited by examiner

*Primary Examiner* — Gary W Counts
(74) *Attorney, Agent, or Firm* — James C. Lydon

(57) ABSTRACT

A separation-free assay including a binding partner, a binding partner labeled with a directly luminescent label, and a non-specifically binding label able to affect the signal of the unbound labeled binding partner, in which a signal of the binding partner label or the signal of the nonspecific binding label is measured in a binding event, and where at least one of the binding partners is a mobile binding partner.

11 Claims, 8 Drawing Sheets

US 8,956,877 B2

SEPARATION-FREE ASSAY METHOD

This application is a continuation-in-part of International Application PCT/FI2007/000042, filed Feb. 21, 2007, which claims benefit under 35 U.S.C. §119 of U.S. provisional application 60/774,608, filed Feb. 21, 2006 and Finnish patent application 20060166, filed Feb. 21, 2006.

FIELD OF THE INVENTION

This invention relates to a method determining concentration of a substance using nonspecifically binding label.

BACKGROUND OF THE INVENTION

The publications and other materials used herein to illuminate the background of the invention, and in particular, cases to provide additional details respecting the practice, are incorporated by reference.

Drug and population screenings have become an essential part of the studies and diagnosis towards improved medical treatment and health care. Within the past two decades, biotechnology has transformed the pharmaceutical industry by providing detailed insights into disease processes and increasing number of drug targets. High-throughput screening technologies (HTS) for large compound libraries have emerged which has resulted in promising early-stage drug candidates. In theory, the wealth of new disease data and the abundance of early-stage assay hits from HTS programs should result in more drugs reaching the market. In practice, however, the pharmaceutical industry is failing to turn potential into profit, and only a small number of promising compounds will make it successfully through development. In order to be competitive, e.g. in finding leads in target molecule screening, rapid, efficient, cost-effective and simple screening techniques are required. A number of separation-free methods has been developed to meet the demands of ultra high-throughput screening in drug discovery: scintillation proximity assay (SPA, Amersham Biotech), amplified luminescence proximity homogeneous assay (ALPHA, Perkin Elmer Life Science), homogeneous time-resolved fluorescence assay (HTRF, Perkin Elmer Life Science and Schering), lanthanide fluorescence energy transfer assay (LANCE, Perkin Elmer Life Science), fluorescence polarization and correlation assays. The impressive list of various technologies includes methods based on radioactive scintillation, fluorescence polarization or correlation and time-resolved fluorescence. Other separation-free methods are also recognized and used in detection of sample substances in a wash-free assay set-up. Two-photon excitation, fluorescence cross-correlation and flow cytometric assay systems are examples of such methods.

The methodologies rely on the use of specific binding substances such as antibodies which recognize the substance of interest with high specificity and affinity. The methods can be used in competitive assay format or cleavage assays where substance is cleaved to separate detection elements and to generate signal. Sandwich type assay systems are often difficult to perform in resonance energy transfer technologies (RET) due to the fact that the detection principle is distance dependent. The distance, in a sandwich type assays, is typically too long to keep donor and acceptor elements close enough to generate adequate signal. Moreover, many of the technologies require labeling of different binding partners with different labeling agents. This may be extremely cumbersome and expensive.

In order to reduce background problems related to many assay technologies, a number of techniques has been developed. In RET assays, reduced or non-existing spectral overlap of donor and acceptor has been proposed (U.S. Pat. No. 6,245,514, U.S. Pat. No. 5,998,146). An efficient way of reducing background signal in an assay system is the use of highly specific and high affinity labeled capture probes against non-bound reaction substances. First specific binding partners are allowed to react and, thereafter, masking is performed using highly specific and high affinity capture quenching elements against non-bound binding partners (US 2004/0253593, U.S. Pat. No. 4,256,834, U.S. Pat. No. 4,404, 366). The affinity of a high affinity interaction is thought to be above $1\times10^7$ $M^{-1}$ and below $1\times10^7$ $M^{-1}$ for low affinity interaction (Journal of Endocrinology, 2002, 175, 121). There are number of optical reduction methods which rely on particle carriers. In these methods, a specific signal is expressed on the particles. Detection is then carried out in a small volume containing the particle(s). Therefore, the background signal can be reduced drastically by sorting particles into the detection volume and carefully selecting the size of the detection volume (U.S. Pat. No. 6,177,277, U.S. Pat. No. 5,981,180, Clinical Chemistry 1997:43; 1749-56, Analytical Chemistry 2000:72; 5618-24, Analytical Biochemistry 1999:271; 143-51). A surface and optical reduction method in combination with dyes has also been investigated. In this method, a non-bound labeled binding partner is quenched using nonspecific dyes. A specific signal is expressed on an immobile, typically essentially flat, solid surface and a quenching component is used to reduce the signal in the solution starting from the vicinity of the surface toward the solution. The quenching component is used to limit the light penetration in the solution. The quenching molecules are used to narrow the thickness of the light penetration depth as excitation light is directed through the immobile solid surface into the solution and the signal towards the excitation light is monitored through the immobile solid surface. The method requires a immobile solid surface and very specific detection geometry in combination with a soluble dye molecule in solution. The method is performed in a separation-free assay format on a solid phase. Winkler has studied protein interaction of fluorochromes and used solution-based quenching mechanism to obtain separation-free fluorescence detection (Biochemistry, 1969:8; 2586). The investigation has been performed for studying interaction of a fluorochrome and proteins. The methodology used is not suitable for assay purposes. Jenkins et al have shown how DNA ruthenium intercalating compounds can be nonspecifically attached to DNA (Biochemistry 1992:31; 10809). Non-attached intercalating compounds are quenched in solution using $Fe(CN)_6^{4-}$. Intercalation takes place through nonspecific interactions after nucleic acid hybridization. None of the nucleic acid strands are being labeled with the intercalating compound and, therefore, the intercalation compound is considered a nonspecific binder without prior coupling to a carrier molecule—in this case coupling to one of the nucleic acid strands.

Many of the abovementioned methods such as ALPHA, HTRF, LANCE and fluorescence correlation assays are suitable for small molecule assay formats but the methods are very cumbersome or impossible to develop for whole cell assaying. The distance dependence or focal restrictions limit the use of the methodologies. Fluorescence polarization can be used for whole cell assaying of typically above 1 nM concentrations of sample substance.

OBJECT AND SUMMARY OF THE INVENTION

One object of the present invention is to provide a separation-free assay method.

The present invention provides a separation-free assay method employing a binding partner label and a nonspecifically binding label, wherein a signal from said binding partner label or said nonspecifically binding label is measured in a binding event, said method comprising the use of
a) two or more binding partners, and a directly luminescent label adsorbed and/or covalently coupled to at least one of said binding partners; and
b) said nonspecifically binding label, wherein
   i) said nonspecifically binding label is able to affect the signal of said binding partner label, or
   ii) said binding partner label is able to affect the signal of said nonspecifically binding label; and wherein
at least one of said binding partners is a mobile binding partner and at least one other of said binding partners is a labeled ligand.

BRIEF DESCRIPTION OF THE DRAWINGS

FIG. 1A demonstrates a sandwich type immunoassay performed on a solid immobile flat surface using a single label approach. Excitation light is directed and emission light is monitored through the flat solid surface. Luminescence of surface-bound and non-bound label cannot be distinguished. FIG. 1B demonstrates the same sandwich type assay performed using an additional nonspecific quenching molecule in solution. The luminescence is quenched in the solution and the luminescence of surface-bound and non-bound label can be distinguished.

FIG. 2A demonstrates how a labeled ligand reacts with a receptor on a cell. Upon addition of quenchers luminescence of non-bound labeled ligands is quenched. Luminescence between bound and non-bound labeled ligand can be distinguished in solution. FIG. 2B demonstrates how a competitive binding partner competes with the receptor binding site. As the concentration of the competitive binding increases less luminescence signal is monitored because luminescence of labeled ligand is quenched in solution.

DETAILED DESCRIPTION OF THE INVENTION

Definitions and Preferred Embodiments

Figure 1A:
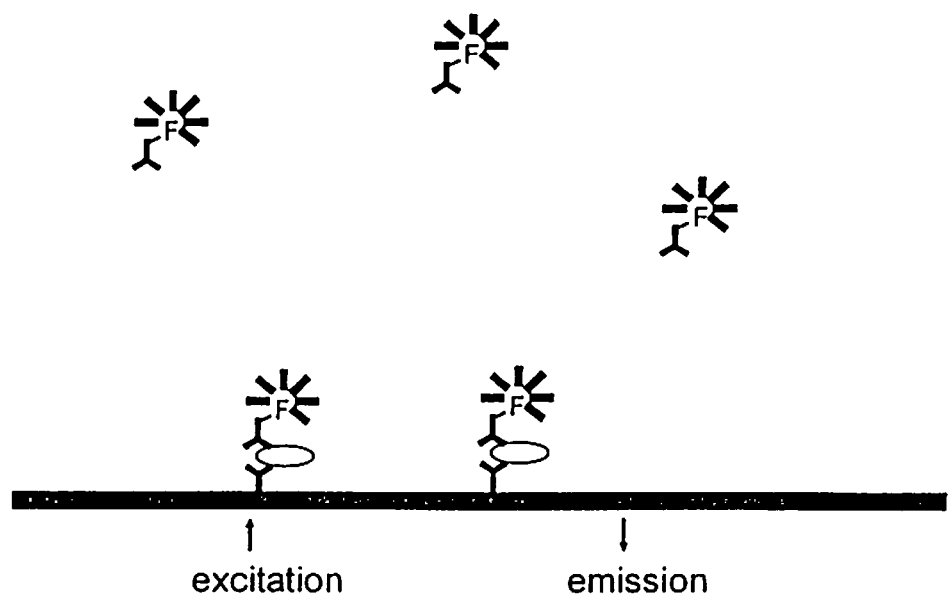
FIGS. 1A and 1B illustrate a state-of-the-art method using nonspecific quenching molecules.
Figure 1B:
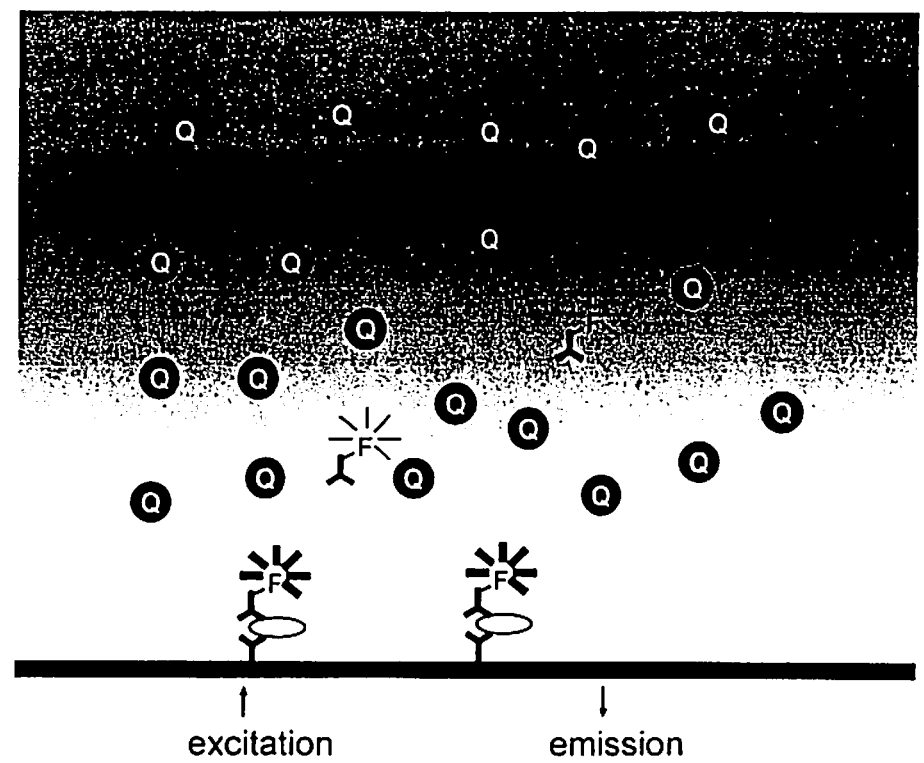
Figure 2A:
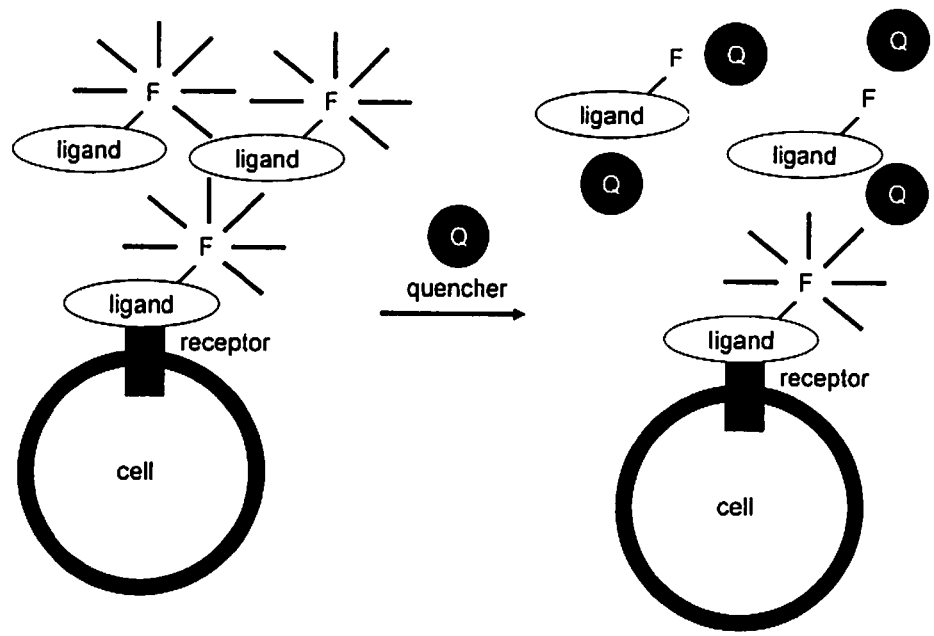
FIGS. 2A and 2B illustrate a luminescence quenching assay according to the invention.
Figure 2B:
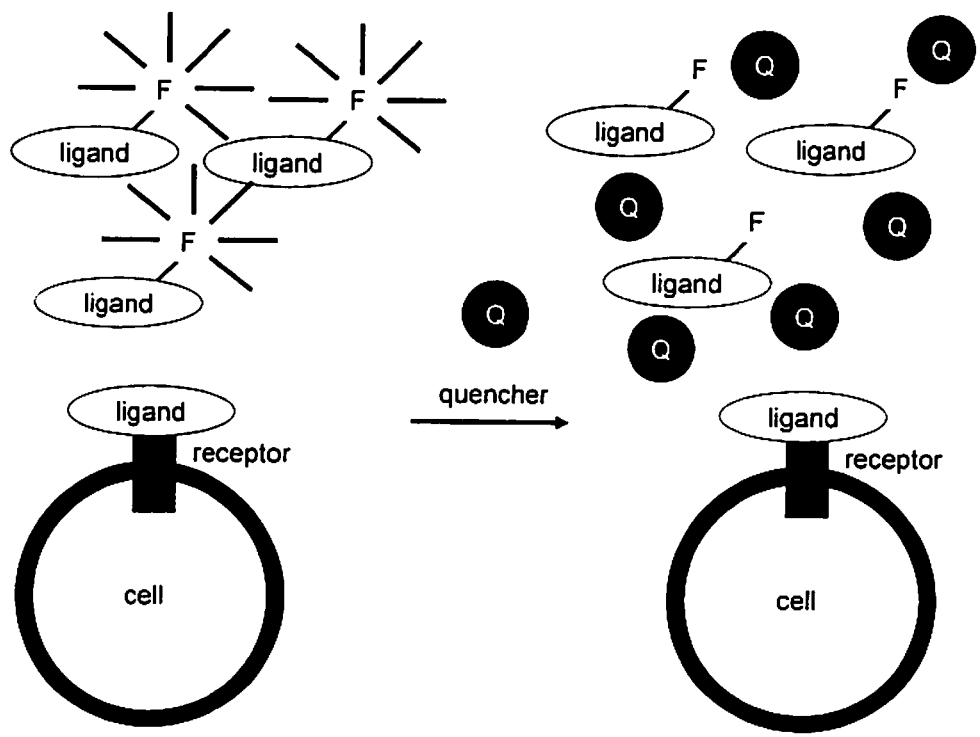
Figure 3:
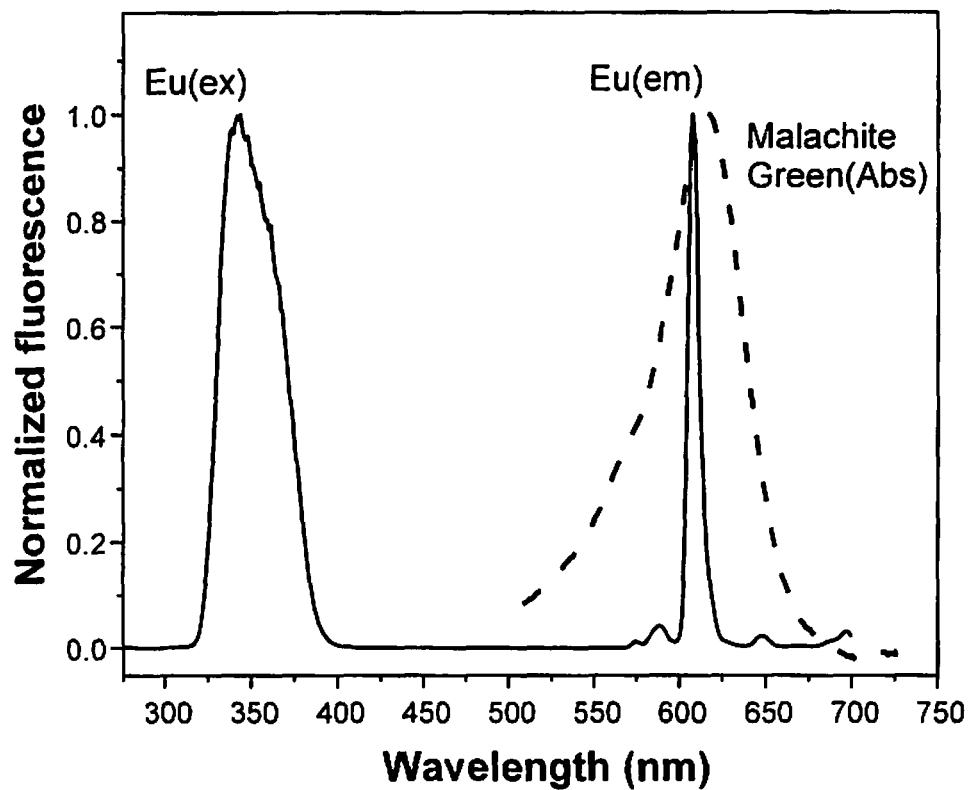
FIG. 3 illustrates the spectra of a europium(III) label and Malachite Green. Malachite Green is a strong quencher of the luminescence signal of the europium(III) label as overlapping of the emission wavelengths of the europium(III) label and absorption of Malachite Green is significant.

It is known that labeled capture-molecules highly specific toward non-bound donor-labeled ligands are used to reduce fluorescence background. The reduction is based on the resonance energy transfer principle. In addition, a method where a label is excited and emission is monitored through an immobile, typically essentially flat, solid surface, in combination with quenching molecules in solution is used to reduce fluorescence background signal. Also a method, where a fluorochrome is intercalated between nucleic acid strands and remaining intercalating compound not capable of attaching in between double-stranded nucleic acid is quenched in solution using ionic compounds, is known. The intercalating compound is intercalated nonspecifically without any prior attachment to either of the nucleic acid strands. The principle requires DNA hybridization before attachment. A method, where chemiluminescence is utilized as a detection principle and non-protected substrate compounds are being quenched, is known. Chemiluminescence is determined as a detection principle where chemical reaction is a mandatory step for signal generation. The detection principle has, therefore, a very different mechanism for signal generation from directly luminescent compounds or fluorochromes. None of the prior art quenching detection principles applies the mechanisms for protein assays. The present invention utilizes nonspecifically binding label molecules and separation-free assay principle together with mobile binding partners in solution in order to successfully reduce background signal. The present invention differs from the prior art technologies in that no labeled high-specific capture molecules are used to reduce background signal, reduction of light penetration depth on a immobile solid surface using quenching molecules is not utilized, the label is attached to the probing compound (binding partner label) prior to reaction or interaction with a mobile binding partner and the label used is directly luminescent.

The following methods are examples of assay methods, which can be applied in the present invention:

Any photoexcited luminescence method can be used according to the present invention. The fluorochromes should be directly luminescent. The fluorochromes are photoexcited luminescent compounds, substances, proteins, polymers, particles, ions or molecules. Luminescence should be understood to comprise at least conventional fluorescence, phosphorescence, gated fluorescence (time-resolved fluorescence) and any directly luminescence mode according to the methods described in Topics in Fluorescence Spectroscopy by J. P. Lakowicz (Plenum Press or Springer, New York, published in multiple volumes starting from 1991). Therefore chemiluminescene and bioluminescence cannot be considered to function according to the principles of the present invention because the methods are not utilizing the principle of direct luminescence. The invention relates to a method where quenching and/or enhancement of direct luminescence are applied.

When quenching is applied, any element can be used to quench a signal such as a dye or metal. In such a case, typically the signal is detected at the emission wavelength of a fluorochrome. Typical metal chelating or complexing agents or ligands used in time-resolved fluorometry are 3-(2-thienoly)-1,1,1-trifluoroacetone, 3-benzoyl-1,1,1-trifluoroacetone, coproporphyrins, porphyrins, 3-naphthoyl-1,1,1-trifluoroacetone, 2,2-dimethyl-4-perfluorobutyoyl-3-butanone, 2,2'-dipyridyl, phenanthroline, salicylic acid, phenanthroline carboxylic acid, aminophenanthroline, diphenylphenantroline, dimethylphenanthroline, bipyridylcarboxylic acid, aza crown ethers, trioctylphosphine oxide, aza cryptands, dibenzoylmethane, dinaphtoylmethane, dibiphenoylmethane, benzoylacetonato, phenylazodibenzoylmethane, dithienylpropanedione, 4,4'-bis(N,N-dimethylamino)benzophenone, tris(6,6,7,7,8,8,8-heptafluoro-2,2-dimethyloctane-3,5-dione, (alkyloxyphenyl)pyridine-2,6-dicarboxylic acid and their derivatives. Metal ions can be, for example, lanthanide or ruthenium ions. (Selvin P. Nature Struc. Biol. 2000:7; 730; Förster T. Discuss. Faraday Soc. 1959:27; 7; Latva M. Academic Dissertation, University of Turku, Finland, 1997; Mukkala V.-M. Academic Dissertation, University of Turku, Finland, 1993; Wöhrle D. and Pomogailo A. D. Metal Complexes and Metals in Macromolecules, John Wiley & Sons, 2003)

Signal reduction may occur through e.g. excited state reactions, molecular rearrangements, energy transfer, complex formation, and static, dynamic or collisional quenching. Quenching is often heavily dependent on pressure and temperature. This can be applied to enhance signal reduction effects. Any of the signal reduction methods described in Principles of Fluorescence Spectroscopy (J. P. Lakowicz, Kluwer Academic/Plenum Publishers, New York, 1999) and Topics in Fluorescence Spectroscopy (J. P. Lakowicz, Plenum Press or Springer, New York, published in multiple volumes starting from 1991) can be utilized according to the invention.

The term resonance energy transfer relates to a method, where a donor compound is in a close vicinity to an acceptor compound. This generates an energy flow from the donor to the acceptor leading to a detection scheme where a signal is monitored through the donor or acceptor. Such a method is well known for example in a luminescence resonance energy transfer system where the donor dye can be a down or up converting dye. The donor is excited and as a consequence of the proximity principle the acceptor dye is excited by the donor compound and a signal is detected at the emission wavelength of the acceptor compound. There are a number of resonance energy transfer methods such as fluorescence, phosphorescence, time-resolved fluorescence, bioluminescence and luminescence resonance energy transfer. The resonance energy transfer can be realised as a signal generating method or a method where the signal is quenched. In the case of quenching, any element can be used to quench signal such as a dye or metal. In such a case, typically the emission wavelength of the donor molecule is detected. Typical metal chelating or complexing agents or ligands used in time-resolved fluorometry are 3-(2-thienoly)-1,1,1-trifluoroacetone, 3-benzoyl-1,1,1-trifluoroacetone, coproporphyrins, porphyrins, 3-naphthoyl-1,1,1-trifluoroacetone, 2,2-dimethyl-4-perfluorobutyoyl-3-butanone, 2,2'-dipyridyl, phenanthroline, salicylic acid, phenanthroline carboxylic acid, aminophenanthroline, diphenylphenantroline, dimethylphenanthroline, bipyridylcarboxylic acid, aza crown ethers, trioctylphosphine oxide, aza cryptands, dibenzoylmethane, dinaphtoylmethane, dibiphenoylmethane, benzoylacetonato, phenylazodibenzoylmethane, dithienylpropanedione, 4,4'-bis(N,N-dimethylamino)benzophenone, tris(6,6,7,7,8,8,8-heptafluoro-2,2-dimethyloctane-3,5-dione, (alkyloxyphenyl)pyridine-2,6-dicarboxylic acid and their derivatives. Metal ions can be, for example, lanthanide or ruthenium ions. (Selvin P. Nature Struc. Biol. 2000:7; 730; Förster T. Discuss. Faraday Soc. 1959:27; 7; Latva M. Academic Dissertation, University of Turku, Finland, 1997; Mukkala V.-M. Academic Dissertation, University of Turku, Finland, 1993; Wöhrle D. and Pomogailo A. D. Metal Complexes and Metals in Macromolecules, John Wiley & Sons, 2003)

The term luminescent oxygen channeling immunoassay refers here to a method where light-induced singlet oxygen is being transferred from its host compound or matter to an acceptor compound or matter when a singlet oxygen host and an acceptor are in a close vicinity to one another. Typically a particle donor and acceptor are used in the method. (Ullman E. F. et al. Clin. Chem. 1996:42; 1518)

Scintillation proximity assay relates to any method where a radioactive label is in close vicinity to matter, which is capable of transforming radioactive emission to light or other form of detectable signal. The matter can be a particle or solid-support. (Hart H. E. et al. Mol. Immunol. 1979:16; 265, Bosworth N et al. Nature 1989:341; 167)

Two-photon excitation is a method, which relies on a small detection volume. The small volume delimits detection from the surrounding medium allowing separation-free assay format. In the method, the dyed substance is bound to a solid-phase particle on which the concentration of the sample substance of interest is detected. Alternatively dyed substance can be bound to a cell or no solid-phase is required. (Hanninen P. et al. Nature Biotech. 2000:18; 548)

Coincidence assay format is an assay concept where two differently dyed particles are coated with e.g. antibodies. As an analyte molecule couples two differently dyed particles together, the presence of the analyte is being measured by detecting the presence of both dyed particles in a small volume. For example, two-photon excitation can be used to reduce the detection volume and separate the two-particle complex from the surrounding medium without any physical separation. The method also allows a concept where only one dyed particle is or no particles at all are being used. The particles can be replaced with soluble dyed substances. (Heinze K. G. Biophys. J. 2002:83; 1671, Heinze K. G. Biophys. J. 2004:86; 506)

Fluorescence polarization assay refers to a method where polarization property of a dyed molecule is altered upon contact with another molecule. When the small dyed molecule is freely moving and rotating in medium, a low polarization value is measured because movement and rotation occurs fast. When the small dyed molecule is attached to a larger molecule such as to a particle or a protein, its polarization is altered and a larger polarization value is measured. (Park S. H. et al. Methods Mol. Biol. 2004:261; 161)

Fluorescence correlation spectroscopic assay can be constructed using a particle and a dyed substance. When the dyed substance is being attached to the particle its fluorescence fluctuation pattern alters leading to a change in signal from that of a freely fluctuating dyed substance. The method does not require particles. Proteins or cells or other larger molecules or molecule complexes can also be utilized. (Krichevsky O. at al. Rep. Prog. Phys. 2002:65; 251)

Flow cytometric assay is a separation-free assay format where particles or cells are used as a solid-support and dyed substance is attached on the surface of the particle or the cell. Thereafter, the extent of dyed substance is being detected through a flow cytometric system. The particles used are typically labeled with fluorochromes to identify each particle. (Fulton R. J. et al. Clin. Chem. 1997: 43; 1749)

Enzyme-based assay relates to an assay format where enzyme or substrate has been attached on a compound or particle or solid-support. Soluble substrates or enzymes reacts with its binding partner generating a detectable signal.

Electron-based method can be constructed using a group capable of releasing or receiving an electron. For example, substances labeled with ruthenium complexes are allowed to compete with a sample substance. When the labeled substance is in close vicinity to an electrode, light is generated as the ruthenium complex undergoes a redox cycle. In another example, a lanthanide chelate labeled substance is allowed to compete with a sample substance. When the labeled substance is in a close vicinity to an electrode, light is generated. (Kenten J. H. Non-radioactive Labeling and Detection of Biomolecules. Springer Berlin, 1992; 175, Knight A. W. Trends Anal. Chem. 1999:18; 47)

Scattering material refers to particles, for example gold or silver particles, and, when referring to surface-enhanced Raman scattering material, it can refer to, e.g. gold or silver particles coated with luminescent molecules such as cyanine dye. Such scattering material can be used to recognize a sample substance nonspecifically or specifically when coated with a receptor. (Ni J. et al. Anal. Chem. 1999:71; 4903, Schultz S. Proc. Natl. Acad. Sci. U.S.A. 2000:97; 996)

Conducting metal particles have typically resonance effects. These resonance effects can be utilized according to the invention to obtain a measurable signal. For example, the resonance effects of silver or gold nanoparticles can be used to enhance the luminescence signal of fluorochromes close to the surface of the particles. A sample substance can affect this signal when nearing the surface or when adsorbed onto the surface. (Geddes C. D. et al. J. Fluor. 2002:12; 121)

Absorptive substance method is based on a molecule which is capable of absorbing energy. Upon binding a change in absorption property is detected. The methodology can be further improved by affecting the absorption property of the non-bound absorptive substance.

The mobile binding partner can be, for example, an antibody; a cell; a receptor on a cell; any receptor, a bacterium; a virus; a cell, viral, bacterial, liposome or vesicle surface substance or protein; a solid phase capable of moving in solution; a polymeric substance; vesicle; liposome; a nucleic acid; any carbohydrate compound; a small molecule; a hapten; a protein; an electrolyte; a substrate; an antigen; or an enzyme. The list of mobile binding partners is not limited to examples given above. Characteristic for this binding partner is that it is mobile or alternatively immobilized on a mobile solid phase. A mobile binding partner should be understood as an entity capable of moving in solution or gas.

The labeled ligand refers to a ligand bearing a label and being able to bind to the mobile binding partner directly or through other binding partners. The ligand of the labeled ligand can be, for example, an antibody; a cell; a receptor on a cell; any receptor; a bacterium; a virus; a cell, viral, bacterial, liposome or vesicle surface substance or protein; a solid phase capable of moving in solution; a polymeric substance; any carbohydrate; a nucleic acid; a small molecule; a hapten; a protein; an electrolyte; a substrate; an antigen; or an enzyme. The list of labeled ligand is not limited to examples given above.

The nonspecifically binding label shall be understood to include the label as such; the label attached to a molecule, to a biomolecule, to a solid particle or to a solid surface. Thus, the nonspecifically binding label can be in dissolved form, in suspended form or in solid form. The label of this component shall have the ability to affect the label of the labeled ligand or the label of the labeled ligand shall have the ability to affect the nonspecifically binding label. The wording "nonspecifically binding" means that this component does not bind at all to the mobile binding partner, to the labeled ligand or to a competing binding partner; and/or the binding has low affinity toward the mobile binding partner, the labeled ligand or the competing binding partner; and/or the component has no specificity to the mobile binding partner, to the labeled ligand or to a competing binding partner. The concentration of the nonspecifically binding label is typically from 0.1 nM to 1 M, preferably from 10 nM to 10 mM, more preferably from 100 nM to 1 mM or even more preferably from 1 to 100 μM. The nonspecifically binding label can be attached, for example, to an antibody; a cell; a receptor on a cell; any receptor; a bacterium; a virus; a cell, viral, bacterial, liposome or vesicle surface substance or protein; a solid phase capable of moving in solution; a polymeric substance; any carbohydrate; a nucleic acid; a small molecule; a hapten; a protein; an electrolyte; a substrate; an antigen; or an enzyme. The list of binders with nonspecifically binding label is not limited to examples given above.

The competing binding partner can be, for example, an antibody; a cell; a receptor on a cell; any receptor; a bacterium; a virus; a cell, viral, bacterial, liposome or vesicle surface substance or protein; a solid phase capable of moving in solution; a polymeric substance; any carbohydrate; a nucleic acid; a small molecule; a protein; an electrolyte; a substrate; an antigen; or an enzyme. The list of competing binding partner is not limited to examples given above.

The binding partner label shall be understood as a label adsorbed or covalently coupled to at least one of the binding partners. The binding partner of this label can be the mobile binding partner, the labeled ligand or the competing binding partner.

The binding partner shall be understood as any binding component or substance. Such a binding partner can be, for example, the mobile binding partner, the labeled ligand, the competing binding partner or any binding component or substance interacting with another binding component.

Nonspecificity is determined as follows: The nonspecifically binding label contains no specific binders to the labeled ligand. For example, an antibody selectively binds to an antigen or a group of antigens with high affinity. Such a binding event is considered specific. Specific binders recognize their ligands, analogues of the ligands and structures very similar to the ligand with high affinity—typically higher than $10^7$ $M^{-1}$ (affinity constant) and/or specific binders have high selectivity towards their ligands, analogues of the ligands and structures very similar to the ligand.

"Sample" refers to an aliquot wherefrom the sample substance or sample substances are to be analyzed. The "sample" can consist of the sample substance or substances as such or with a carrier.

"Sample substance" refers to a substance or substances to be analyzed, i.e. sample substance or substances. The sample may contain solely a single substance. A sample substance can be anything with a maximum diameter below 100 000 nm. The sample substance may appear in any form such as an organic or inorganic substance, an agglomerate, a vesicle, a liposome, a particle or a dyed particle, an antibody; a cell; a receptor on a cell; any receptor; a bacterium; a virus; a cell, viral, bacterial, liposome or vesicle surface substance or protein; a solid phase capable of moving in solution; a polymeric substance; any carbohydrate; a nucleic acid; a small molecule; a hapten; a protein; an electrolyte; a substrate; an antigen; or an enzyme. The list of binders with nonspecifically binding label is not limited to examples given above. Alternatively the sample substance may appear in mixtures of above-mentioned substances. Yet the sample substance may appear in a fragmented or disintegrated form where for example larger units, such as cells, are partially or totally broken into fragments or parts of said units. The sample substance can also be a biomolecule on a surface of any structure such as virus, bacterium, cell, vesicle, liposome, particle, polymer or any substance. The sample substance to be analyzed may inherently contain a signal element such as luminescent or colour group, substrate for enzyme or the sample substance can be, for example, a luminescent protein or particle. The sample substance can be, for example, the mobile binding partner, the labeled ligand, the competing binding partner or any binding component or substance interacting with another binding component. Preferable the sample substance is the competing binding partner.

A separation-free assay format is an assay format where the solution of the reaction is not physically separated from the solid phase. A separation-free method allows a dilution of the solution of the reaction and a transfer of the solution of the reaction within the entire reaction and/or detection vessel or system but no physical separation of the solution and solid phase is allowed.

The method according to the invention can be a non-competitive assay.

Preferred embodiments of the invention are competitive assays typically comprising a competing binding partner, expected to bind to the mobile binding partner.

The label of the binding partner preferably is a donor or an acceptor of a label pair.

The nonspecifically binding label is preferably a quencher, an enhancer, an acceptor of a donor-acceptor label pair, or a donor of a donor-acceptor label pair.

The signal of the labeled ligand, bound to the mobile binding partner, is preferably enhanced or quenched by adding a separate enhancer or quencher respectively, being capable of binding to the mobile binding partner.

The signal of the labeled ligand, both bound and/or non-bound to the mobile binding partner, is preferably enhanced by adding an enhancer, being capable of binding to or interacting with the labeled ligand.

The directly luminescent label of the binding partner is preferably a donor of a label pair, and nonspecifically binding label is preferably a quencher, more preferably a soluble quencher.

The label of the labeled ligand preferably comprises a lanthanide.

The label pair can be a resonance energy transfer label pair, is preferably a luminescence resonance energy transfer label pair, and the donor is preferably a lanthanide or ruthenium chelate.

The invention comprises a common feature with different detection methods. Therefore, the method according to the invention can be applied in various methods. For example, in a simple receptor-ligand assay, the ligand (labeled ligand) is labeled with a fluorochrome. In such a case the ligand-specific receptor (mobile binding partner) may or may not be labeled. The mobile binding partner and the labeled ligand are allowed to react. In order to obtain signal from the binding event, a quencher molecule (nonspecifically binding label) is added to the solution before, after or simultaneously with the receptor-ligand binders. Quenching occurs between non-bound fluorochrome-labeled ligand and nonspecifically binding quencher label molecule. Typical is that labeled high-specific capture-molecules toward non-bound fluorochrome-labeled ligands are not used to reduce the background signal and a fluorochrome is directly attached to ligand through adsorption or using covalent chemistry. It should be noted that the present invention does not relate to the use of an immobile solid surface in combination with quenching molecules in solution to reduce the background signal. Embodiments of the invention using quenching molecules can be used in luminescent oxygen channeling immunoassays, two-photon excitation assays, coincidence assays, fluorescence polarization assays, fluorescence correlation spectroscopic assays and flow cytometric assays. Alternatively luminescence can be increased in the solution using luminescence enhancing substances or luminescence can be altered using luminescence resonance energy transfer principle.

Instead of a simple receptor-ligand binding assay, a competitive assay can be performed using the method of the invention. A competing binding partner, a mobile binding partner and a labeled ligand are mixed together with a non-specifically binding label in any order. The competing binding partner competes with the labeled ligand for the binding site of the mobile binding partner. The signal of the bound and/or non-bound labeled ligand is altered by the nonspecifically binding label. Therefore, the concentration of the competing binding partner can be measured.

According to some preferred embodiments, the method of invention can be used to determine concentration of a sample substance in an immunoassay, a receptor-ligand assay, an enzyme-substrate reaction, a nucleic acid detection system or any test system having binding partners. The assays can be competitive or non-competitive. The nucleic acid assay system can rely, for example, on a polymerize chain reaction, hybridization assay, a combination of polymerize chain reaction and a subsequent hybridization assay, or an extension, a cleavage or a ligation method.

According to some preferred embodiments, the assay components can be dried into a reaction vessel and suspended upon addition of a solution which may or may not contain a sample substance.

Figure 7:
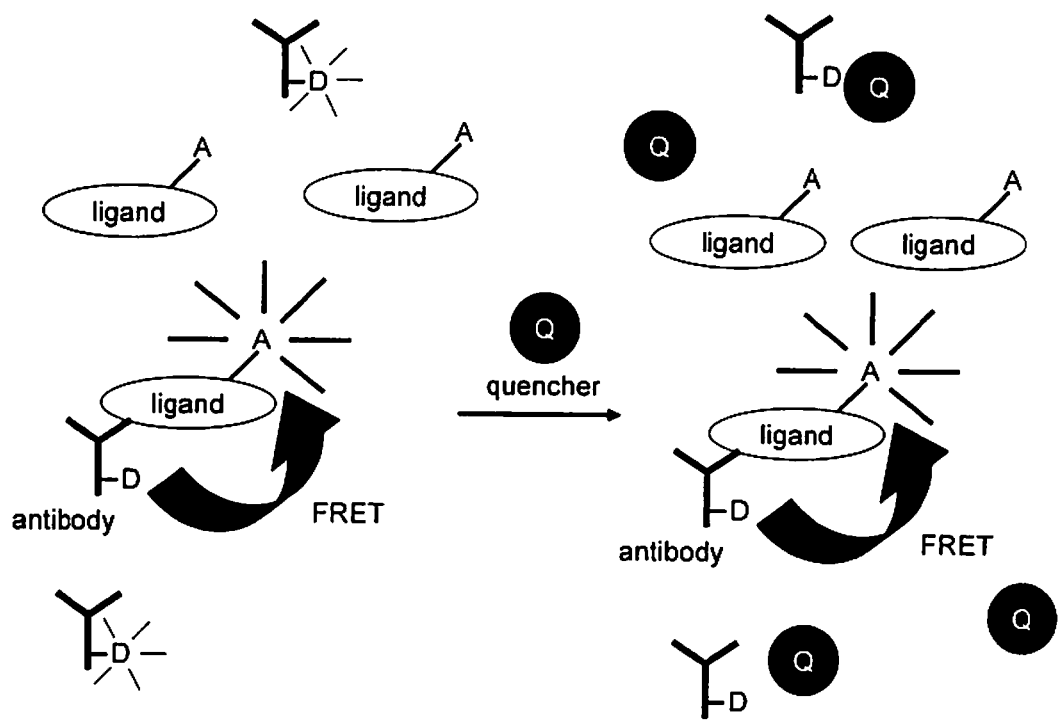
FIG. 7 illustrates an alternative luminescence resonance energy assay according to the invention. A donor labeled receptor reacts with an acceptor labeled ligand. Upon addition of soluble quencher molecules background signal originating from non-bound donor and/or acceptor molecules is quenched improving the signal-to-background ratio of the assay.

Any of the binding partners can be labeled. For example, in a competitive RET assay, a ligand or receptor can be labeled with a donor or an acceptor. Moreover, an assay system can comprise multiple dye, donor or acceptor molecules which may undergo multiple energy or electron transfer processes. Therefore, more than one label molecule can be attached to the binding partners and ligands. This is the case, for example, in a luminescence resonance energy transfer assay where a binding partner is labeled with a donor or acceptor molecule and a ligand with an acceptor or donor molecule, respectively (FIG. 7). Typical is that one of the labels is directly luminescent. The nonspecifically binding label can affect these excitation and/or emission pathways. The binding partners should be labeled with a label using adsorption and/or covalent chemistry strategies. Multiple intercalating compounds can interact with nucleic acid double strands. In such an assay scheme typically none of the nucleic acid strands is labeled using adsorption and/or covalent chemistry. The intercalating compound binds in between the strands nonspecifically and it is therefore structure-specific and requires the formation of the structure in order to be able to bind in between strands. It is advantageous not to label any of the strands as more intercalating compound can be attached to the nucleic acid strands.

The method of invention can be applied to measure sample substances such as cells, bacteria, viruses, polymers, agglomerates, antibodies, receptors, ligands, nucleic acids, small molecules, solid phases capable of moving in solution, polymers, carbohydrates, substrates, enzymes, haptens, electrolytes or proteins and receptors, ligands, nucleic acids, small molecules, carbohydrates, polymers, antibodies, substrates, haptens, electrolytes or proteins inside or on a surface of viruses, bacteria or cells. In fact, problems related to the measurement of surface components on viruses, bacteria or cells with the state-of-the-are methods can be circumvented according to the present invention. For example, in a RET-based assay both donor and acceptor molecules must bind within a few nanometer distances from one another. This may be a difficult task or even impossible to accomplish on viruses, bacteria or cells. According to the invention, using single labeling strategy and a nonspecifically binding label, viruses, bacteria or cells can be assayed. The sample substance to be analyzed may inherently contain a signal element such as a luminescent or color group, substrate for enzyme; or the sample substance can be, for example, a luminescent protein.

In preferred embodiments the nonspecifically binding label can be a soluble label, a particle label, a label combined with a carrier such as particle or protein, a combination of two or more labels, a biomolecule label such as luminescent protein, an organic label, an inorganic label, ionic or non-ionic compounds or a mixture of the above-mentioned labels. In addition, the nonspecifically binding label can be a surface or a part of a surface. Said nonspecifically binding label can be directed toward the labeled ligand, or any labeled binding partner in order to reduce, retain or enhance the signal. The signal which is affected with the nonspecifically binding label can be further reduced or enhanced by adding a signal reducer or enhancer, respectively, being capable of binding to or interacting with the nonspecifically binding label.

Alternatively said nonspecifically binding label can be directed, for example, toward the excitation light in order to reduce, retain or enhance a signal. For example, in a RET assay, a nonspecific quencher molecule can be directed toward the wavelengths of excitation and/or emission light of the donor and/or acceptor in order to reduce the signal. According to one alternative, the nonspecifically binding label can be directed toward a bound and/or non-bound labeled ligand. For example, in a competitive RET assay, a nonspecifically binding quencher molecule can reduce luminescence signal of a labeled small molecule or a labeled receptor molecule.

The signal quencher (total or partial quenching) or enhancer can be, for example, any fluorochrome, absorbent, luminescent protein, a non-labeled binding partner, ionic or non-ionic compounds, any light/energy, electron, or oxygen absorbing group or it can be an agglomerate or particle containing any fluorochrome, absorbent, luminescent protein, a non-labeled binding partner, ionic or non-ionic compound, any light/energy, electron, radioactivity or oxygen absorbing group. The alternatives are dependent on the method used. The interaction between the labeled ligand or any labeled binding partner and nonspecifically binding label can be non-existing or physical or chemical. Typical is that no labeled highly specific capture biomolecules are used.

According to one embodiment, the label of the ligand can be any compound capable of generating a measurable signal directly without any need for a chemical or biochemical reaction before signal generation, for example, a short-lived or long-lived fluorochrome, a biomolecule label such as a luminescent protein, a light absorbing substance, a substrate, an electron releasing or receiving substance, a singlet oxygen releasing or receiving substance. This is dependent on the method used.

According to one embodiment, the signal of the labeled ligand may be affected upon binding with its binding partner, the mobile binding partner. The signal may be increased or decreased depending on the labeled ligand and the binding partner. For example, a labeled small molecule binds to a receptor. Upon binding, the signal of the labeled small molecule increases (FIG. 8). This can be, for example, a result of a reduced number of quenching water molecules in the vicinity of said labeled small molecule or any other alternative effect.

Figure 4A:
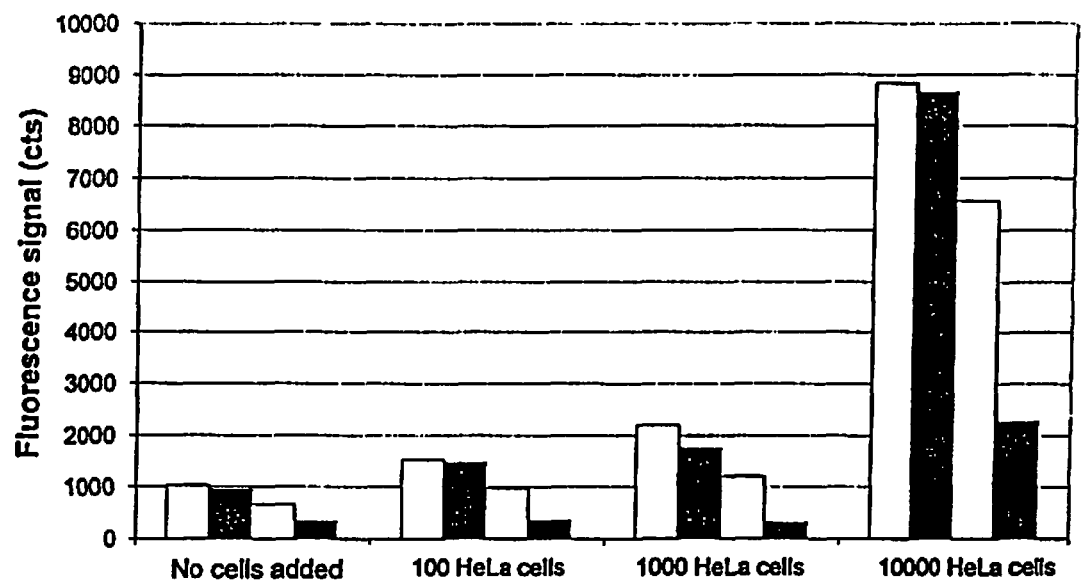
FIGS. 4A and 4B illustrate a competitive assay of estradiol (from left to right in each set of bars: 0, 0.1, 1 and 100 nM of estradiol) employing an europium(III)-labeled estradiol and an estradiol antibody. Different numbers of HeLa cells were incubated with the binding partners. Malachite Green was used to quench the luminescence signal of the non-bound europium(III)-labeled estradiol in solution. A refers to the luminescence signal and B to the normalized luminescence signal of the assays.
Figure 4B:
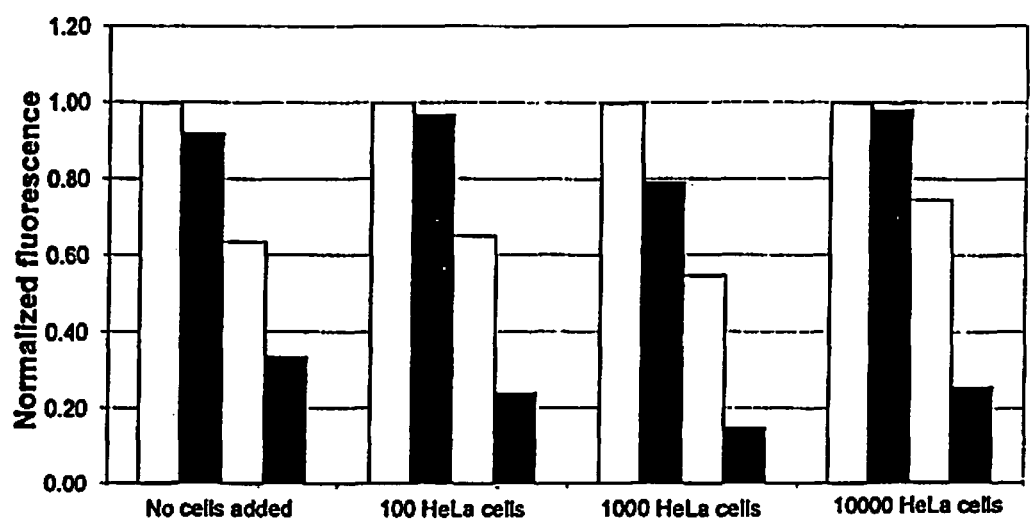
Figure 5:
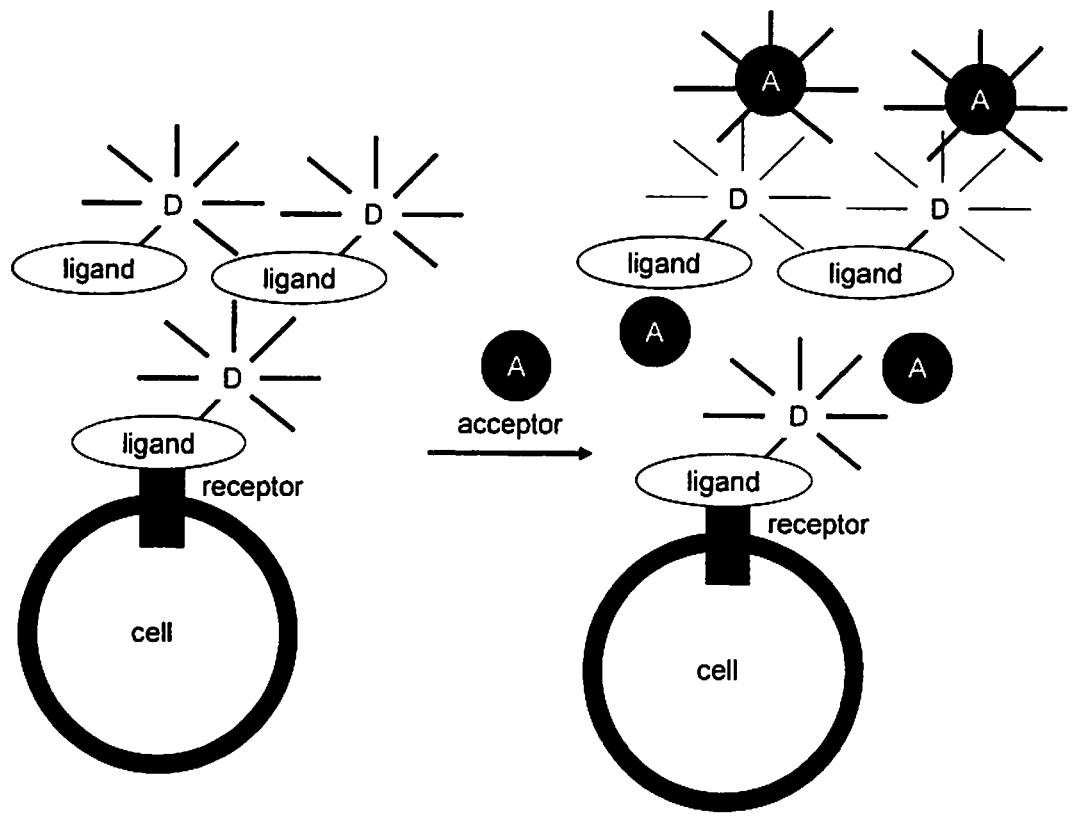
FIG. 5 illustrates a luminescence resonance energy assay according to the invention. A donor labeled ligand reacts with a receptor on a cell. Upon addition of soluble acceptor molecules a luminescence resonance energy transfer signal of non-bound donor labeled ligands is obtained. Increase in the luminescence resonance energy transfer signal in solution correlates to the number of receptors.
Figure 6:
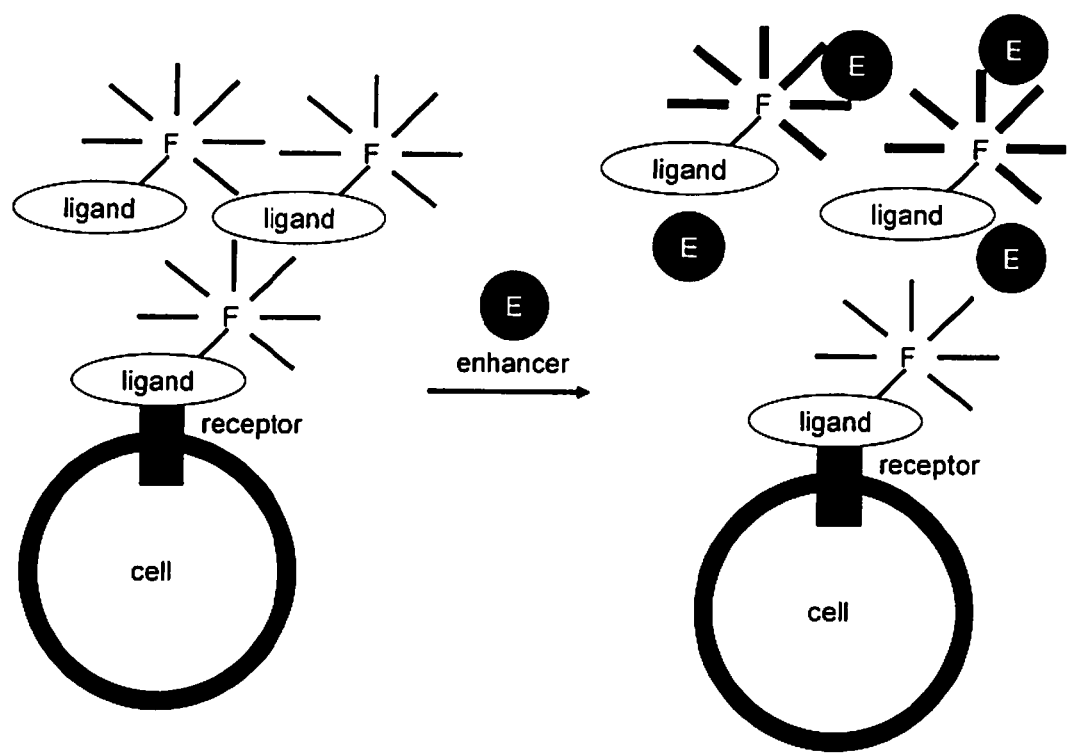
FIG. 6 illustrates a luminescence enhancing assay according to the invention. A labeled ligand reacts with a receptor on a cell. Upon addition of a soluble enhancer molecule the luminescence signal of the non-bound labeled ligand is increased.

According to one embodiment, the signal of the bound and/or non-bound labeled substance may be affected upon interacting with a specific or nonspecific binding partner. The signal may be increased or decreased depending on the said labeled ligand and the specific or nonspecific binding partner. For example, in a competitive assay, bound and/or non-bound labeled small molecules interact with an additional specific or nonspecific binding partner. Upon binding, the signal of the labeled small molecule increases. Still upon addition of a nonspecifically binding label molecule, the signal of the bound and/or non-bound labeled small molecule bound to an additional specific or nonspecific binding partner is affected. In FIG. 4, cells act as such nonspecific binding partners because the luminescence signal of the bound and non-bound labeled small molecule increases upon addition of cells. This allows reduction of the number of binding partners in the test system improving the detection limit of the test system. The specific or nonspecific binding partner may be, for example, an antibody; a cell; a receptor on a cell; any receptor; a bacterium; a virus; a viral or bacterial surface substance or protein; a solid phase capable of moving in solution; a polymeric substance; any carbohydrate; a nucleic acid; a small molecule; a hapten; a protein; an electrolyte; a substrate; an antigen; or an enzyme.

According to one alternative, the labeled ligand is protected from the said non-specifically binding label upon binding to a receptor improving the signal-to-background ratio in the assay. For example, a labeled small molecule is less affected by said nonspecifically binding label upon binding to a receptor than in a free non-bound form (FIG. 8). This can be further improved by adding alternative specific or nonspecific binders into to the reaction which increase the signal-to-background ratio. For example, a labeled protein binds to a receptor. Alternative receptors are used to attach to the labeled protein-receptor complex protecting the labeled protein being quenched by the nonspecifically binding label in solution. The receptor in this context may be, for example, an antibody; a cell; a receptor on a cell; any receptor; a bacterium; a virus; a viral or bacterial surface substance or protein; a solid phase capable of moving in solution; a polymeric substance; any carbohydrate; a nucleic acid; a small molecule; a hapten; a protein; an electrolyte; a substrate; an antigen; or an enzyme.

In an assay utilizing the present invention, the order of the assay steps can be selected and varied to obtain optimal signal-to-background ratio. Any assay step order can be chosen. For example, sample substance and labeled small molecule are allowed to compete and bind to a receptor and, thereafter, the nonspecifically binding label is added and a signal is detected. According to the invention, the same assay can be performed by adding all components simultaneously or in any order.

According to an alternative embodiment, the method can be used to calculate the number of cells, viruses or bacteria.

According to one alternative, the method of invention can be used in combination with a methodology determining concentration, charge or unit size of a sample substance. In the methodology a sample and a labeled substance is contacted with a solid phase, wherein the proximity of the labeled substance to said solid phase has the ability to generate a signal. Signal generation occurs when, for example, a labeled ligand is nearing the solid phase or, for example, a sample substance and a labeled ligand are allowed to compete for the vicinity of the solid phase surface. The nearing to the surface of the solid phase of the luminescent compounds in the close vicinity of the solid phase surface increases or reduces luminescence signal, or luminescence energy is transferred between luminescent compound and the solid phase. Above-listed methods can be used to generate a signal for the measurement of concentration, charge or unit size according to the present invention.

Preferably, the method of invention is used to determine the presence of sample substance or substances or the concentration of sample substance or substances, to calculate the number of cells, viruses or bacteria or to determine concentration, charge or unit size in combination with said methodology determining concentration, charge or unit size in a competitive or non-competitive format, preferably in a competitive format.

The method of invention can be applied in solution or gas, preferably in solution.

According to some preferred embodiments, the method can be used to detect the presence of sample molecule in real time.

The method of invention can be used in multiple instrument setups. Whenever the sample substance must be excited with light, different configurations can be used to measure the concentration of the substance successfully. The light source of such a measurement configuration can be, for example, halogen, xenon, tungsten, hydrogen or deuterium lamp or laser or a semiconducting light source such as light emitting diode. The detector can be, for example, a photoemissive, a photomultiplier or a semiconducting detector such as a photodiode. The detecting configuration may be carried out by having the light source on one side of the measurement vessel and the detector on the other side. The light source and detector may well have an angle in between them. An often used setup is an epi-configuration (with a 180 degree angle). Well-known methods such as filters, monochromators, prisms or gratings can be used to select suitable excitation and emission wavelengths for different optical configurations.

According to one alternative, the signal can be detected after the reaction and after drying the reaction components. The signal is typically detected in solution shortly after the incubation. According to the invention, the signal-to-background ratio can be further improved by drying the reaction components after the reaction.

The method according to this invention can be used to measure a sample substance in many various fields such as biology, biochemistry, chemistry, medicine, diagnostics, forensics, military, food industry, paper and pulp industry, and cosmetics. The list of application fields is not limited to examples given above.

ADVANTAGES OF THE INVENTION

The current invention can provide several advantages. The invention can provide a very simple method to determine concentration of a sample of interest. For example, typically a sample, a labeled ligand, a mobile binding partner and a nonspecifically binding label are mixed and the signal is monitored within a short period of time. The method requires labeling of only one of the binding partners contrary to the state-of-the-art methods. Furthermore, the signal is detected in solution and no coupling of specific biomolecules on an immobile solid-surface is required. The method can be applied to nucleic acid and immunoassays as well as to viruses, bacteria or cells. Especially, receptor studies on cells makes the method intriguing as the state-of-the-art methods apply poorly to measuring surface-embedded proteins. Since the method can be used in cell-based assays as well as in traditional immunoassays the versatility of a technology increased compared to the typical state-of-the-art methods. In addition, the sensitivity of the method is typically better than when using conventional fluorescence polarization assays capable of determining receptor concentration on cell surface.

The invention will be illuminated by the following non-restrictive examples.

EXAMPLES

Example 1

Competitive Estradiol Assay Using Estradiol-Specific Antibody

In a microtiter well, 50 µL of estradiol in an assay buffer was added in different concentrations. Thereafter, 50 µL of 3 nM estradiol-specific antibody solution was added and the reaction was allowed to proceed 10 min. Europium(III)-labeled estradiol at 1.25 nM concentration was added in 50 µL of assay buffer. The incubation was carried out for 2 min and 50 µL of nonspecific Malachite Green label solution at 15 µM concentration was added. After 2 min incubation, the europium signal was monitored using commercial Victor II microtiter plate reader (PerkinElmer Life Sciences, Turku, Finland). The signal of the non-bound europium(III)-labeled estradiol was quenched significantly but the signal of the bound europium(III)-labeled estradiol was nearly unaffected. Excitation and emission wavelengths were 340 and 615 nm, respectively and the delay and window time were both 400 µs.

Example 2

Competitive Estradiol Assay Using Estradiol-Specific Antibody and HeLa Cells

In a microtiter well, 50 µL of estradiol in an assay buffer was added in different concentrations. Thereafter, 5 µL of 30 nM estradiol-specific antibody solution and 45 µL of 10 000 HeLa cells were added and the reaction was allowed to proceed 10 min. Europium(III) labeled estradiol at 1.25 nM concentration was added in 50 µL of assay buffer. The incubation was carried out for 2 min and 50 µL of nonspecific Malachite Green solution at 15 µM concentration was added. After 2 min incubation, the europium signal was monitored using the commercial Victor II microtiter plate reader. Excitation and emission wavelengths were 340 and 615 nm, respectively and the delay and window time were both 400 µs (FIG. 4).

Example 3

Competitive Estradiol Assay Using Estradiol-Specific Antibody

Figure 8A:
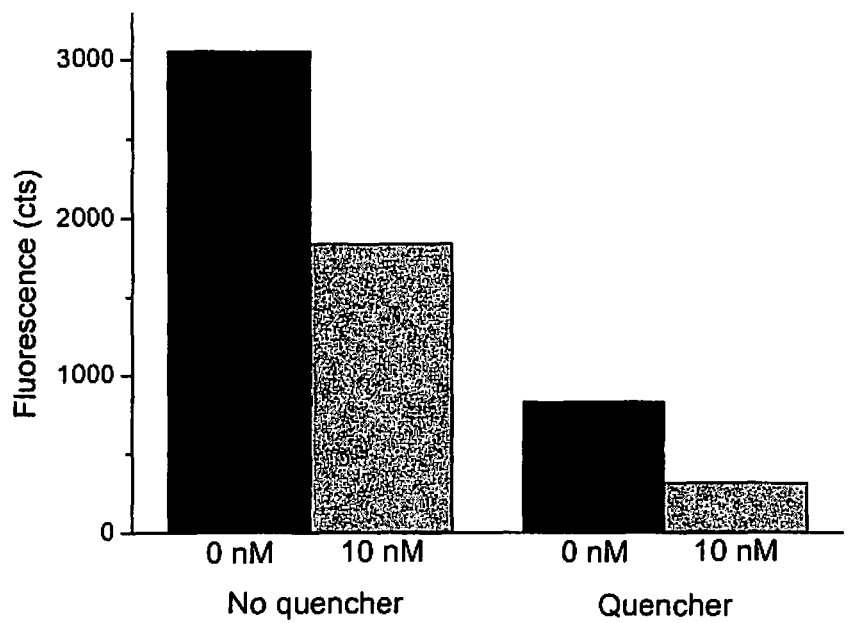
FIGS. 8A and 8B illustrate a competitive assay of estradiol at 0 or 10 nM concentration of estradiol employing an europium(III)-labeled estradiol and an estradiol antibody. Malachite Green was used to quench the luminescence signal of the non-bound europium(III)-labeled estradiol in solution and in comparison no quencher was used. A refers to the luminescence signal and B to the normalized luminescence signal of the assays. Upon binding to the antibody the signal of europium(III)-labeled estradiol was enhanced and protected. Upon adding quencher larger signal-to-background ratio was obtained.
Figure 8B:
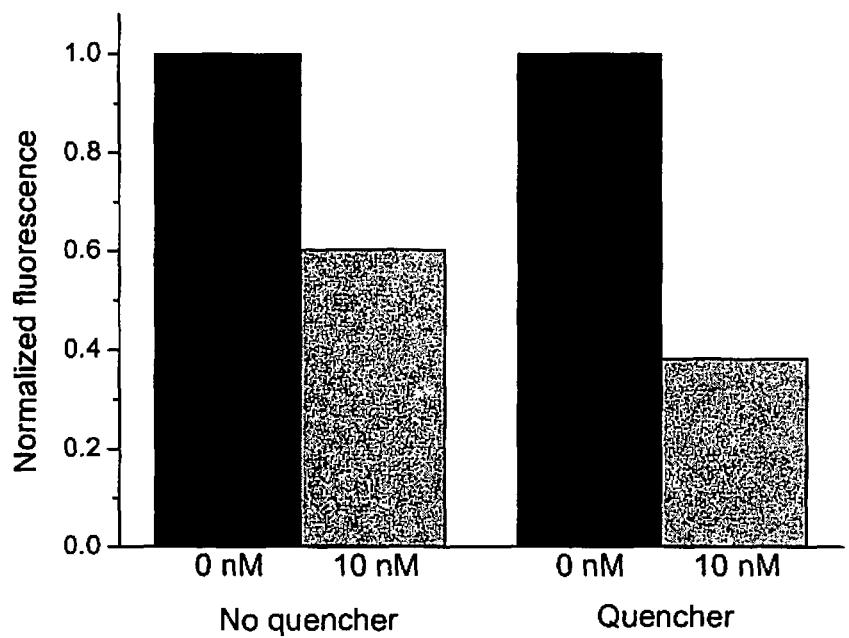

In a microtiter well, 5 µL of estradiol in an assay buffer was added at 0 or 10 nM concentrations. Thereafter, 5 µL of 10 nM estradiol-specific antibody solution was added and the reaction was allowed to proceed 10 min. Europium(III) labeled estradiol at 15 nM concentration was added in 5 µL of assay buffer. The incubation was carried out for 2 min and 5 µL of nonspecific Malachite Green solution at 0 or 10 µM concentrations was added. After 2 min incubation, the europium signal was monitored using the commercial Victor II microtiter plate reader. Excitation and emission wavelengths were 340 and 615 nm, respectively and the delay and window time were both 400 µs (FIGS. 8A and 8B).

It will be appreciated that the methods of the present invention can be incorporated in the form of a variety of embodiments, only a few of which are disclosed herein. It will be apparent for the expert skilled in the field that other embodiments exist and do not depart from the spirit of the invention. Thus, the described embodiments are illustrative and should not be construed as restrictive.

The invention claimed is:

1. A separation-free assay method to determine a concentration of a substance in a sample, the method comprising
 adding a binding partner to said sample,
 allowing the binding partner to bind specifically to said substance,
 adding a labeled ligand having a directly luminescent label adsorbed and/or covalently coupled thereto to said sample,
 allowing the labeled ligand to specifically bind with said binding partner to form a complex with the binding partner,
 adding a nonspecifically binding label to the sample,
 allowing the nonspecifically binding label to affect a signal of unbound, labeled ligand which has not formed a complex with said binding partner,
 measuring directly without separation of said complex or said unbound, labeled ligand from the sample
  a signal of the labeled ligand of said complex, or a signal of said unbound, labeled ligand,
 wherein at least one of said binding partner and said labeled ligand is mobile, and
 determining the concentration of said substance by measuring said signal of the labeled ligand of said complex or measuring said signal of said unbound, labeled ligand.

2. The method according to claim 1 wherein the method is a non-competitive assay.

3. The method according to claim 1 wherein the method is a competitive assay, the method further comprising
 adding a competitive binding partner, and
 allowing the competitive binding partner to bind to the binding partner that is mobile.

4. The method according to claim 1, wherein the label of the binding partner that is mobile is an acceptor of a donor-acceptor label pair or a donor of a donor-acceptor label pair.

5. The method according to claim 1, wherein the nonspecifically binding label is a quencher, an enhancer, an acceptor of a donor-acceptor label pair, or a donor of a donor-acceptor label pair.

6. The method according to claim 1, the method further comprising
 adding a separate enhancer or quencher to said sample, the separate enhancer or quencher being configured to enhance or quench the signal of the labeled ligand upon binding to the binding partner that is mobile.

7. The method according to claim 1, the method further comprising
 adding an enhancer to said sample, the enhancer being configured to enhance the signal of the labeled ligand upon binding to or interacting with the binding partner that is mobile.

8. The method according to claim 1, wherein the label of the labeled ligand is protected from the nonspecifically binding label upon binding to a binding partner that is a receptor.

9. The method according to claim 4, wherein the label pair is a resonance energy transfer label pair.

10. The method according to claim 4, wherein the label of the labeled ligand comprises a lanthanide.

11. The method of claim 1, wherein the signal of said labeled ligand is increased or decreased upon binding of said labeled ligand to said binding partner.

* * * * *